United States Patent [19]
Tadir et al.

[11] Patent Number: 5,458,595
[45] Date of Patent: Oct. 17, 1995

[54] VAGINAL SPECULUM FOR PHOTODYNAMIC THERAPY AND METHOD OF USING THE SAME

[75] Inventors: Yona Tadir, Irvine; Michael W. Berns, Trabuco Canyon; Brad J. Monk, Long Beach; Glen Profeta, Rancho Santa Margarita; Bruce J. Tromberg, Irvine, all of Calif.

[73] Assignee: The Regents of the University of California, Oakland, Calif.

[21] Appl. No.: 168,553

[22] Filed: Dec. 16, 1993

[51] Int. Cl.[6] ............................................. A61B 17/32
[52] U.S. Cl. ............................. 606/15; 606/14; 600/220
[58] Field of Search ........................... 128/3; 606/2, 3, 606/7, 14, 15, 16, 17

[56] References Cited

U.S. PATENT DOCUMENTS

| | | | |
|---|---|---|---|
| 3,278,738 | 10/1966 | Clark | 606/140 X |
| 4,616,631 | 10/1986 | Takahashi | 128/6 |
| 5,026,368 | 6/1991 | Adair | 606/15 |
| 5,125,925 | 6/1992 | Lundahl | 606/15 |
| 5,179,937 | 1/1993 | Lee | 606/14 X |
| 5,242,437 | 9/1993 | Everett et al. | 606/15 |
| 5,242,438 | 9/1993 | Saadatmanesh et al. | 606/15 |

*Primary Examiner*—Peter A. Aschenbrenner
*Attorney, Agent, or Firm*—Daniel L. Dawes

[57] ABSTRACT

An improved vaginal speculum for photodynamic therapy of intraepithelial tissue and in particular vaginal, cervical and vulvar neoplasia utilizes a precisely and accurately positionable optic fiber through which a predetermined dose of light in the range of 620 to 700 nanometers is delivered over a controlled area which has been previously treated with photodynamic therapeutic substances. In particular, the neoplastic area has been treated with hematoporphyrin derivatives and other photosensitizers which are selectively taken into the cancerous tissue. Exposure to the appropriate wavelength laser light photoactivates the absorbed hematoporphyrins causing the release of singlet oxygen which internally oxidizes and ultimately causes cell death. The fiber optic tip from which the laser light is transmitted is precisely positioned within the body cavity at a predetermined distance from the intraepithelial neoplasia in order to obtain the appropriate spot size and location to minimize damage to healthy tissue and maximize damage to the selectively impregnated cancerous tissue.

6 Claims, 2 Drawing Sheets

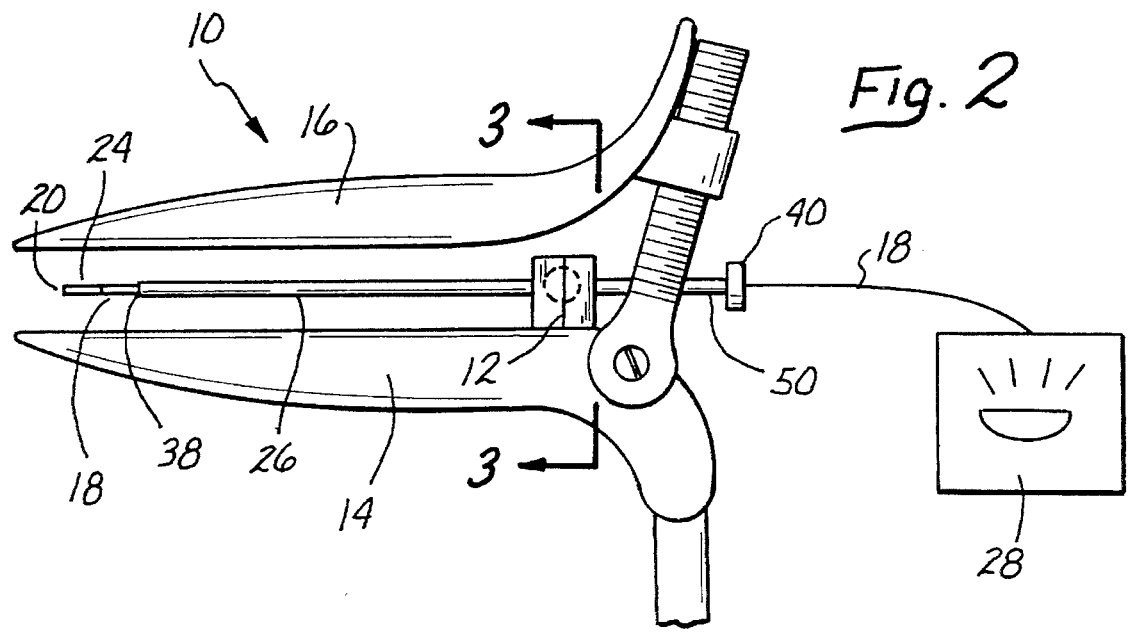
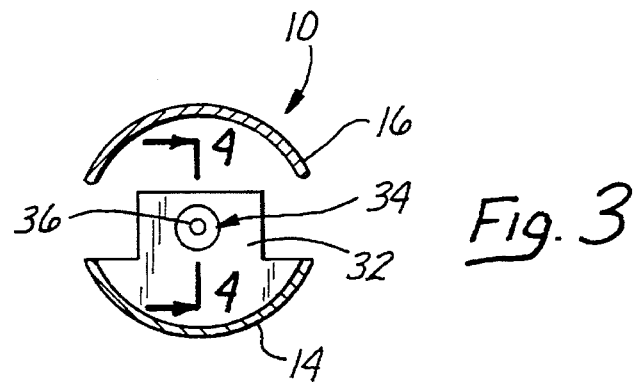
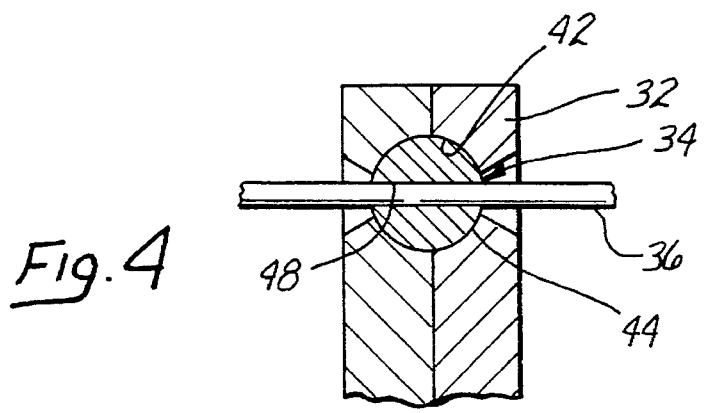

5,458,595

VAGINAL SPECULUM FOR PHOTODYNAMIC THERAPY AND METHOD OF USING THE SAME

This invention was made with Government support under Grant (or Contract) No. N00014-91-C-0134, awarded by the ONR; No. RR01192, awarded by the NIH; and No. DE FG03 91ER61227, awarded by the DOE. The Government has certain rights in this invention.

BACKGROUND OF THE INVENTION

1. Field of the Invention

The invention relates to the field of photodynamic therapy and in particular to a vaginal speculum used for intravaginal photodynamic treatment.

2. Description of the Prior Art

Photodynamic therapy of skin tissues is well known. However, there has been no application of photodynamic therapy for the diagnosis and treatment uterine abnormalities. Premalignant changes of vagina, vulva and cervix occur in untold thousands of females annually in the United States. For reasons which are unknown, the number of new cases which have been detected have steadily risen in the last 10 to 15 years. Intraepithelial neoplasia of the genital tract can occur in various locations in the form of vaginal intraepithelial neoplasia, vulvar intraepithelial neoplasia, and cervical intraepithelial neoplasia.

Conventional treatment of unifocal, small, low grade intraepithelial neoplasia of the genital tract is usually performed using a variety of locally tissue destructive techniques, such as $CO_2$ laser vaporization, cryotherapy, electrocautery, or local excision. In the case of multifocal, large, or high grade intraepithelial neoplasia, more extensive surgical procedures are used, typically skinning vulvectomy, partial vaginectomy or hysterectomy. Radical surgical procedures are deemed necessary not only because of the higher failure rate which has been experienced in the treatment multifocal, large or higher grade intraepithelial neoplasia, when treated with local destruction only, but also particularly in the case of multifocal lesions because of the tendency of those lesions to recur outside of the locally treated area. For this reason, the entire diseased organ must be removed to assure that all microscopic disease is treated. Since the percentage of these lesions that will advance to a frankly malignant state is unknown and may be a minority of instances, indiscriminate destruction or surgical removal of the entire organ is, in fact, a radical and excessive treatment.

Therefore, what is needed is some type of procedure and instrument which can effectively be used in the treatment of vaginal, cervical and vulvar intraepithelial neoplasias without the radical approach of conventional treatments and yet which will be effective.

BRIEF SUMMARY OF THE INVENTION

The invention is an apparatus for providing photodynamic therapy on intraepithelial tissue. The apparatus comprises an instrument for establishing a reference position relative to the intraepithelial tissue. An optical fiber is provided for selectively transmitting light along the optical fiber. A fiber guide is coupled to the instrument, supports and guides the optical fiber into a selected position relative to the intraepithelial tissue. As a result, photodynamic therapy may be practiced on the epithelial tissue with controlled and repeatable exposures of the light transmitted through the optical fiber onto a selected portion of the intraepithelial tissue.

In the illustrated embodiment the instrument is a vaginal speculum. The instrument and fiber guide are made of stainless steel and can also be fabricated preferably from plastic to be disposable. The fiber guide comprises a universal joint and a tube for supporting and holding the optical fiber. The tube is coupled to the universal joint to allow selective positioning of the tube. The optical fiber further comprises a transmitting end and an optical lens coupled to the transmitting end for focusing light transmitted through the optical fiber into a predetermined pattern.

The fiber guide comprises element for permitting longitudinal movement of the optical fiber through the guide to adjust distance between the transmitting end of the optical fiber and the intraepithelial tissue. The fiber guide comprises an element for permitting longitudinal movement of the optical fiber through the guide to adjust distance between the transmitting end of the optical fiber and the intraepithelial tissue. The apparatus further comprises graduations for facilitating positioning of the optical fiber from the intraepithelial tissue by a selected distance.

The universal joint comprises a fixture having a spherical socket defined therein and a ball slidingly disposed and captured within the spherical socket within the fixture. The ball has a bore defined therethrough and the tube is are slidingly disposed through the bore in the ball. The universal joint further comprises an elastomeric element for providing a predetermined degree of friction between the ball and spherical cavity defined in the fixture to permit stable positioning of the tube.

The invention is also a method for providing photodynamic therapy of intraepithelial tissue comprising the steps of selectively impregnating an hematoporphyrin derivative into intraepithelial tissue, and exposing the impregnated tissue to light at a predetermined wavelength to photoactivate the hematoporphyrin derivative in the tissue to cause cell death. As a result, intraepithelial neoplasia is eradicated without radical tissue destruction.

The step of selectively impregnating the intraepithelial tissue comprises the step of repeatedly topically applying the hematoporphyrin derivative over a predetermined time. The step of exposing the intraepithelial tissue to a predetermined wavelength comprises the step of exposing the intraepithelial tissue to light having a wavelength of approximately 620 to 700 nanometers. The step of exposing comprises the step of exposing the intraepithelial tissue to the light with a dose of approximately 40–140 joules per square centimeter.

In one embodiment the step of selectively impregnating the intraepithelial tissue comprises the step of impregnating the tissue with the hematoporphyrin derivative carried in Eucerin cream. In another embodiment the step of impregnating the tissue comprises the step of impregnating the intraepithelial tissue with the hematoporphyrin derivative in a 4 percent by volume Azone ethylnol and water solution. In a preferred embodiment the step of selectively impregnating the intraepithelial tissue comprises the step of impregnating dihematoporphyrin ether into the intraepithelial tissue. Still further the step of selectively impregnating the intraepithelial tissue comprises the step of impregnating hematoporphyrin derivatives in the intraepithelial tissue in which low molecular weight porphyrins less active and photodynamic therapeutic effects have been removed.

The invention is better visualized by turning to the following drawings where like elements are referenced by like numerals.

BRIEF DESCRIPTION OF THE DRAWINGS

FIG. 2 is a simplified side elevational view of the improved speculum of the invention, diagrammatically shown as connected to a laser source.

FIG. 3 is a simplified cross sectional view of the improvement of FIG. 2 as seen through section lines 3—3 of FIG. 2.

FIG. 4 is a perpendicular cross sectional view to the section view of FIG. 3 as seen through section lines 4—4 of FIG. 3.

The invention and its various embodiments may now be better understood by turning to the following detailed description.

DETAILED DESCRIPTION OF THE PREFERRED EMBODIMENTS

An improved vaginal speculum for photodynamic therapy of intraepithelial tissue and in particular vaginal, and cervical neoplasia utilizes a precisely and accurately positionable optic fiber through which a predetermined dose of light in the range of 620 to 700 nanometers is delivered over a controlled area which has been previously treated with photodynamic therapeutic substances. In particular, the neoplastic area has been treated with photosensitizers such as hematoporphyrin derivatives and preferably with dihematoporphyrin ethers like photofrin, ALA. BPD, and phtalocyamies, which are selectively taken into the cancerous tissue. Exposure to the appropriate wavelength laser light photoactivates the absorbed hematoporphyrins causing the release of singlet oxygen which internally oxidizes and ultimately causes cell death. The fiber optic tip from which the laser light is transmitted is precisely positioned within the body cavity at a predetermined distance from the intraepithelial neoplasia in order to obtain the appropriate spot size and location to minimize damage to healthy tissue and maximize damage to the selectively impregnated cancerous tissue.

Figure 1A:
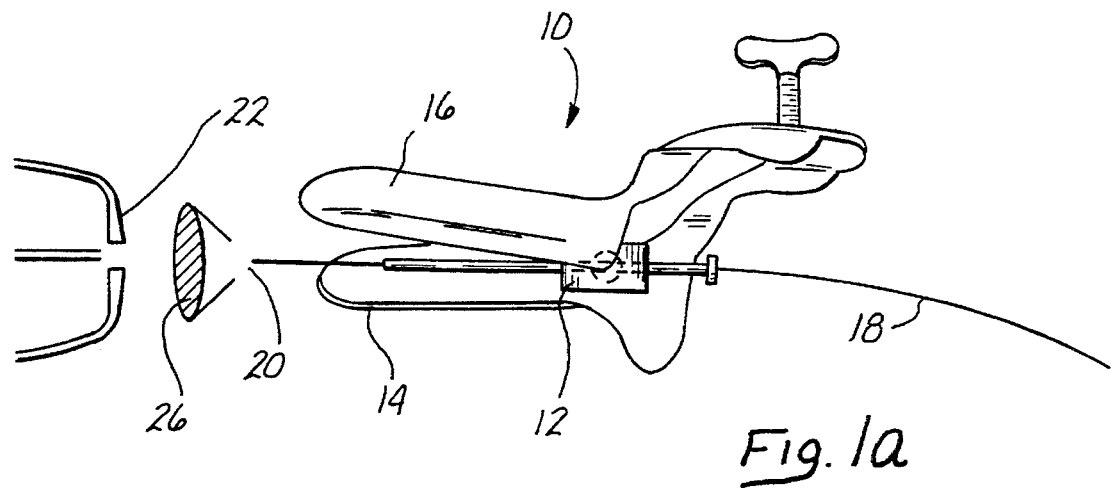
FIGS. 1a, 1b and 1c are simplified diagrammatic partially cut away views of vaginal speculum incorporating an improvement for use in photodynamic therapy according to the invention.
Figure 1B:
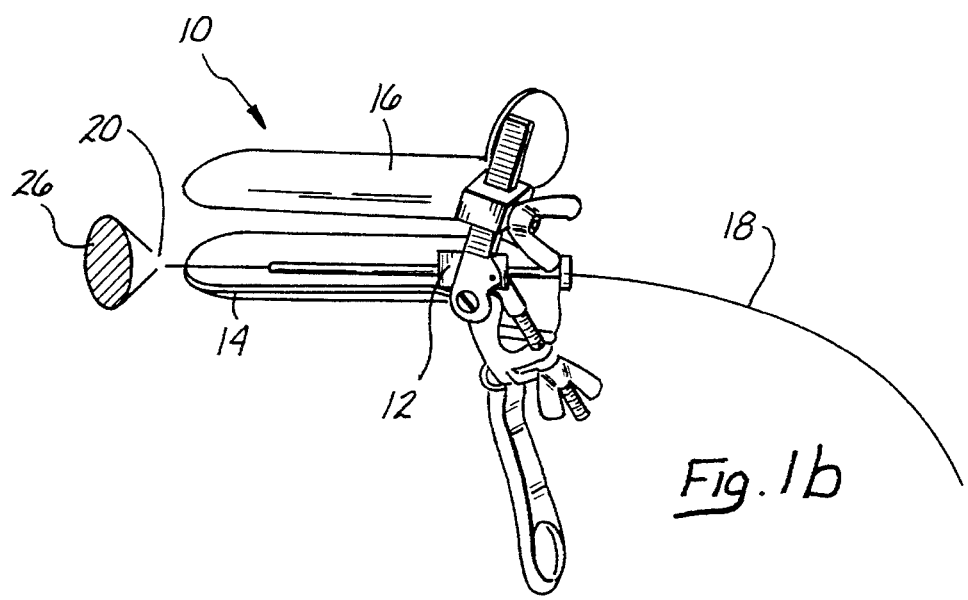
Figure 1C:
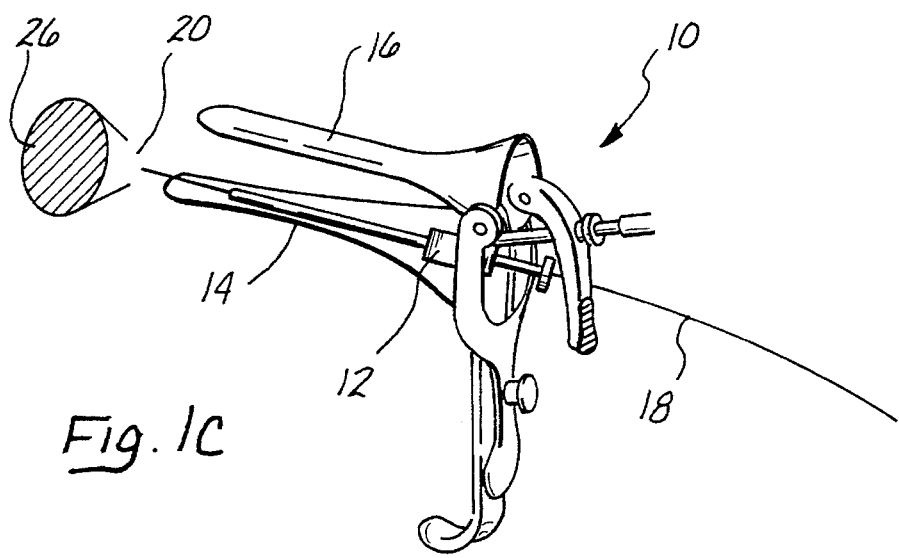

Three conventional vaginal speculums, improved according to the invention, are shown in FIGS. 1a–1c. Similar disposable speculum fabricated from plastic can be applied. The vaginal speculum, generically denoted by reference numeral 10 is provided with a rigidly mounted fiber guide 12 having a movable axis on one of the jaws 14 of speculum 10. In the illustrated embodiment because lower jaw 14 is typically the jaw which is left in position while upper jaw 16 is moved to expand the vaginal opening. A photodynamic fiber 18 is then fed through fiber guide 12 terminating in a tip 20 from which the photodynamic light is emitted onto intraepithelial target 22, which in the diagrammatic depiction of FIG. 1a is a cervix.

Light may be emitted from tip 20 directly from the end of fiber 18 or through appropriate optics, such as a microlens 24, described in greater detail in connection with FIG. 2, to provide a focused cone of light 26. In this way, the area of exposure on target 22 can be accurately and repeatably controlled both through choice of optics 24 and positioning of tip 20 relative to target 22.

Before describing an embodiment of the improved vaginal speculum of FIGS. 1a–1c in greater detail in connection with FIGS. 2–4, it is best to understand the context of the use of the instrument or speculum 10. In the illustrated embodiment, topically applied Photofrin solution is currently used in the treatment of vaginal, cervical and vulvar intraepithelial neoplasias in combination with topical photodynamic therapy. A fixed dose of activated red light is delivered by an argon pumped dye laser system generally denoted in FIG. 2 by reference numeral 28.

Many chemicals in combination with oxygen and visible light have demonstrated cytotoxicity. A photodynamic effect was first noticed with eosin in 1903. In 1972, crude hematoporphyrin was reported to cause regression of experimental gliomos in rats when activated by white light. Subsequent studies have shown that light activated hematoporphyrin derivatives show cytocidal activity in a variety of animals and human tumors with little toxicity to the host.

The cytotoxic agent produced by exposure of hematoporphyrin to light is singlet oxygen. The initial toxic effect of a formation of singlet oxygen in tissue is local vascular collapse with tissue death occurring at a later period. Light within the range of 620 to 700 nanometers is most effective in producing excitation of hematoporphyrin to produce singlet oxygen. Light in the range of 620–700 nm can be effective for excitation of other photosensitizers. Conventional light sources and in particular laser energy sources are well adapted to producing light at this wavelength and with intensities useful for treatment of experimental tumors.

The interpretation and modeling of the phototoxic activity of hematoporphyrin derivatives requires a knowledge of the intracellular binding sites of photosensitizing chemicals. Unfortunately, little is known about the location of photodynamic sensitizers in cell. However, these compounds have been shown to be concentrated in liposomes and cell membranes. Damage to either of these organelles by photosensitive chemicals assure cell death. It is possible that other intracellular binding sites may also exist.

Photosensitizing chemicals, including hematoporphyrin derivatives, are also a class of organic compounds which fluoresce when exposed to ultraviolet light. This property allows localization of the photosensitizing agent in various tissues following administration of the drug. Exposing fluorescent areas to light in the range of 620 to 700 nanometers elicits a cytotoxic photodynamic effect.

Radiolabel studies of carbon 14-labeled hematoporphyrin derivatives have shown that following injection of the drug, a maximum uptake of about 4 milligrams per kilogram of a syngeneic mouse tumor was noted 3 to 24 hours post injection of 10 milligrams per kilogram. The corresponding level uptake in normal skin is about 3 to 4 milligrams of hematoporphyrin derivatives per gram.

The usefulness of hematoporphyrin derivatives and other chemicals exhibiting a photodynamic effect lies in its ability to selectively accumulate and/or be retained in neoplastic tissue. The small amount of hematoporphyrin derivatives that is present in normal tissue is responsible for the most commonly observed human toxicity—skin sensitive to sunlight following administration. This difference is sufficient to yield a very high therapeutic index ratio. Discrimination of this type between normal and neoplastic tissue is desirable since even a highly focused light source will show some scattering beyond the desired treatment area when directed at living tissue. The cellular mechanism of preferential hematoporphyrin derivative concentration in neoplastic tissue is, however, not well understood.

In an attempt to eliminate the only serious known side effect of systematic hematoporphyrin derivative administration, which is generalized cutaneous photosensitivity, the illustrated embodiment employes a topical preparation of Photofrin that contains 4 percent Azone by volume in ethanol/water (50:50) and a penetration-enhancing agent, which delivers the drug directly to the disease site without providing systematic levels to produce skin photosensitivity. Topical formulations of this type have been previously used in experimental treatment of psoriasis.

Animal model studies indicate that there is a selective retention of hematoporphyrin derivatives in areas of chemically induced squamous dysplasia after topical application of hematoporphyrin derivatives. Skin tumors were produced in mice by intraperitoneal administration of urethane followed by regular topical application of 12-O-tetradecanoyl-phorbol-13-acetate (TPA). These tumors presumably passed through a phase of cutaneous intraepithelial neoplasia and, therefore, can be used as an in vivo model for testing the efficacy of the photodynamic effect in the treatment of these lesions.

The concentration of hematoporphyrin derivatives in areas of cutaneous epithelial neoplasia in higher relative amounts than in normal tissues results in several advantages. First, premalignant epithelial lesions can be treated through nonsurgical essentially nontoxic means. Second, the disadvantage of limited tissue penetration of light does not apply since intraepithelial lesions are typically less than 3 to 4 nanometers in depth. This is well within the depth of tissue penetration normally seen with light in the range of 620 to 700 nanometers. Third, large areas of multiple areas of intraepithelial neoplasia can be located and mapped by taking advantage of the fluorescent characteristic of hematoporphyrin derivatives, thereby precluding the need for multiple biopsies to show the extent of the disease.

On the basis of animal model studies, which have demonstrated the effective topical delivery and selective concentration in premalignant epithelial lesions, the methodology has been applied in the case of human epithelial neoplasia in the female genital tract. In the pilot study in question, all patients had failed conventional attempts at control of their disease. A topical application of DHE (photofrin) lyophilized powder (1%) is incorporated into a vehicle in either a Eucerin cream or an ethanol/water (50:50) vehicle containing sterile water, USP 48%, isogropanol 48%, azone 4% (1-dodecylazacyclohelptane-2-1, pharmaceutical grade. Azone in an ethanol/water (50:50) vehicle was applied to the treatment area 24 hours prior to photodynamic therapy. The treatment areas as well as the 2 to 4 centimeter rim of surrounding clinically uninvolved tissue was exposed to light of approximately 630 nanometers provided through an argon ion pumped dye laser. The light dose to each treated lesion was 40–100 joules per square centimeter. Follow-up examinations were performed one week after treatment and at three month intervals.

According to the protocol, drug dose in fixed and light does is gradually increased in 20 $J/cm^2$ increments. The initial four patients received the lowest dose of light (40 $J/cm^2$). One patient exhibited disease progression within three months and was treated in a conventional modality. One patient demonstrated slow regression from CIN I–II to normal colposcopy with few dysplastic cells in the PAP smear, and two patients exhibited no disease at three months following treatment. All patients are still being followed. The second group of four patients received 60 $J/cm^2$ of light and at three months no disease was evident in the two patients, except for microscopic dondyloma in the biopsy. Two other patients, one of which was CIN III had few dysplastic cells at three months. A third group of patients was treated with 80 $J/cm^2$ and only one CIN III patient reached the first follow up at three months in which normal colposcopy and cytology were demonstrated. The first patient in the 100 $J/cm^2$ group was recently treated and additional patients will be treated with 100, 120 and 140 $J/cm^2$. The preliminary evidence shows favorable responses of cervical intraepithelial neoplasia with the Azone vehicle and effective topical penetration.

Return now to the description of the device used in the above treatment. FIG. 2 is a side cross sectional view of the conventional speculum 10, such as shown in FIG. 1c, improved according to the invention. Fiber guide 12 is affixed to lower jaw 14, preferably at or near handle 30 of lower jaw 14. Fiber guide 12 is comprised of a rigid fixture 32 into which a universal or ball joint 34 has been fitted. A hollow tube 36 is then disposed through ball joint 34 and acts as a guide and support tube for optic fiber 18. Optic fiber 18 is telescopically disposed through guide tube 36 and has its tip 20 extending from distal end 38 of tube 36. A conventional microlens 24 capable of shaping or focusing the light beam can be provided on tip 20 on the end of optic fiber 18. Only the tip-most portion of optic fiber 18 extends from guide tube 38 so that it is substantially supported and positioned in accordance with the position of distal end 38 of guide tube 36.

Guide tube 36 in turn is slidingly disposed through ball joint 34. Proximate end 40 of tube 36 is provided with a knob which allows the physician to firmly manipulate guide tube 36 within ball joint 34. Thus, guide tube 36 may be rotated around any axis disposed through ball joint 34 and may be longitudinally inserted or withdrawn through ball joint 34 by pushing or pulling on proximate end 40. In this way, tip 20 of fiber optic 18 may be positioned accurately at any position in the body cavity, and usually within the opening provided by jaws 16 and 14 speculum 10. Rotation of tip 20 is restricted only by limited angles of movement permitted by ball joint 34, which is more graphically illustrated in connection with the cross section of ball joint 34 shown in FIG. 4. However, in practice, limitations of rotation inherent in ball joint 34 are never encountered, and movement is first limited either by jaws 14 and 16 of speculum 10 or by the inner walls of the body cavity.

Greater detail of fixture 32 can be seen in connection with the cross sectional views of FIGS. 3 and 4. FIG. 3 is a cross sectional view taken through section 3—3 of FIG. 2 just behind proximate end 40 of tube 36. Fixture 32 in the illustrated embodiment is affixed to lower jaw 14 through recessed bolts (not shown). Fixture 32 then has an upper portion which extends to the axis of speculum 10, leaving tube 36 approximately in the center of the working area provided by speculum 10.

The longitudinal cross sectional view of FIG. 4, taken through section lines 4—4 of FIG. 3 shows the perpendicular cross section of fixture 32 and tube 36. Fixture 32 is manufactured so that it is split in the center with a spherical cavity 42 defined therein to receive ball 44. Both halves of fixture 32 are then fixed together by means of screws thereby capturing ball 44 within ball joint 34. Ball 44 may be seated intimately within spherical bearing cavity 42.

Tube 36 is also slidingly disposed through a longitudinal bore 48 defined through ball 44. Bore 48 may be defined to provide frictional contact with the outer walls of tube 36, or an innerlying elastomeric frictional collar or other means may also be disposed within bore 48 to enhance or provide a controlled frictional engagement between the two. However, the frictional engagement of tube 36 to ball 44 or ball 44 to fixture 32 is never so great as to prohibit movement of tube 36 with relative ease and to permit its precise positioning through fine finger control.

In the use of speculum 10, the target-to-tip distance must be carefully adjusted in order to provide the appropriate exposure area and incident exposure intensity. In the illustrated embodiment, an applicator or measurement stick is inserted through the positioned speculum to physically measure the distance through contact from the target to fixture 32. Alternatively, fiber 18 can be withdrawn so as to bring tip 20 within distal end 38. Tube 36 itself is longitudinally disposed to provide target contact which can either be felt or observed.

Once the fixture-to-target distance is established for a specific patient, tube 36 can be longitudinally positioned within ball joint 34 to provide the appropriate tip-to-target 22 spacing. To facilitate this, a series of graduations 50 can be defined on tube 36 extending from proximate end 40 to ball joint 34 and slightly beyond allowing direct observation and measurement of the extent to which tube 36 is inserted in or withdrawn from ball joint 34. The markings or graduations 50 may, in fact, be calibrated directly in terms of fixture-to-target separation to allow the physician to read off the distance directly from graduations 50.

The distance which tip 20 must be spaced from the target is determined according to the exposure area desired. The exposure area is determined through the fluorescent examination as described above. The target-to-tip distance in order to obtain the desired target area is then experientially determined by creating a laser exposure area on a blank screen equal to the desired area for photodynamic therapy. The experientially determined distance needed to obtain the desired exposure area is then noted and re-created within fiber guide 12 of the invention when speculum 10 is placed in position within the patient. The same procedure could also be calculated with known optical performance of the fiber and optical lens.

In the illustrated embodiment, speculum 10 and fiber guide 12 has been shown as made of metal, but it is expressly understood and contemplated that speculum 10 and fiber guide 12 may be made of plastic or other disposable materials. It is intended that the entire device will be made of inexpensive materials and disposable, including the portion of the optic fiber 18 which may be used in the procedure.

It should also be understood that although the device has been described in connection with the use in feminine genital tract in combination with a speculum that the same concepts can be employed with other types of devices and fixtures for the treatment intraepithelial tissue. Therefore, exposure levels, optic wavelengths, specific optics used in combination with the device and method can all be varied without departing from its spirit and scope.

Many alterations and modifications may be made by those having ordinary skill in the art without departing from the spirit and scope of the invention. Therefore, it must be understood that the illustrated embodiment has been set forth only for the purposes of example and that it should not be taken as limiting the invention as defined by the following claims. The following claims are, therefore, to be read to include not only the combination of elements which are literally set forth, but all equivalent elements for performing substantially the same function in substantially the same way to obtain substantially the same result. The claims are thus to be understood to include what is specifically illustrated and described above, what is conceptionally equivalent, and also what essentially incorporates the essential idea of the invention.

We claim:

1. An apparatus for providing photodynamic therapy on intraepithelial tissue comprising:

a vaginal speculum for establishing a reference position relative to said intraepithelial tissue;

an optical fiber for selectively transmitting light along said optical fiber; and a fiber guide having a longitudinal elongated axis coupled to said speculum for supporting and guiding said optical fiber into a selected position relative to said intraepithelial tissue for permitting controlled and measured longitudinal movement of said optical fiber through said guide to adjust distance between said transmitting end of said optical fiber and said intraepithelial tissue, whereby photodynamic therapy may be practiced on said epithelial tissue with controlled and repeatable exposures of said light transmitted through said optical fiber onto a selected portion of said intraepithelial tissue.

2. An apparatus for providing photodynamic therapy on intraepithelial tissue comprising:

an instrument for establishing a reference position relative to said intraepithelial tissue;

an optical fiber for selectively transmitting light along said optical fiber; and a fiber guide coupled to said instrument for supporting and guiding said optical fiber into a selected position relative to said intraepithelial tissue, wherein said fiber guide comprises a universal joint and a tube for supporting and holding said optical fiber, said tube being coupled to said universal joint to allow selective positioning of said tube, whereby photodynamic therapy may be practiced on said epithelial tissue with controlled and repeatable exposures of said light transmitted through said optical fiber onto a selected portion of said intraepithelial tissue.

3. The apparatus of claim 2 wherein said fiber guide comprises means for permitting longitudinal movement of said optical fiber through said guide to adjust distance between said transmitting end of said optical fiber and said intraepithelial tissue, and further comprising graduations for facilitating positioning of said optical fiber from said intraepithelial tissue by a selected distance.

4. The apparatus of claim 2 wherein said universal joint comprises a fixture having a spherical socket defined therein and a ball slidingly disposed and captured within said spherical socket within said fixture, said ball having a bore defined therethrough and said tube being slidingly disposed through said bore in said ball.

5. The apparatus of claim 4 wherein said universal joint further comprises elastomeric means for providing a predetermined degree of friction between said ball and spherical cavity defined in said fixture to permit stable positioning of said tube.

6. The apparatus of claim 1 wherein said instrument and fiber guide are fabricated from plastic and are disposable.

\* \* \* \* \*